United States Patent [19]

Báder et al.

[11] Patent Number: 4,639,304

[45] Date of Patent: Jan. 27, 1987

[54] APPARATUS FOR DETERMINATION OF ALUMINUM OXIDE CONTENT OF THE CRYOLITE MELT IN ALUMINUM ELECTROLYSIS CELLS

[75] Inventors: Imre Báder; Endre Berecz, both of Miskolc; Gábor Szina; János Horváth, both of Budapest, all of Hungary

[73] Assignee: Nehezipari Muszaki Egyetem, Hungary

[21] Appl. No.: 794,103

[22] Filed: Nov. 1, 1985

[51] Int. Cl.$^4$ .............................................. G01N 27/58
[52] U.S. Cl. ...................................... 204/413; 204/67; 204/422
[58] Field of Search ................. 204/67, 422, 423, 413, 204/1 T, 1 S, 245

[56] References Cited

U.S. PATENT DOCUMENTS 3,471,390 10/1969 Kibby et al. ...................... 204/67 X Primary Examiner—G. L. Kaplan
Attorney, Agent, or Firm—Handal & Morofsky

[57] ABSTRACT

An analytical apparatus for determining the cryolite concentration in a cryolite-alumina electrolysis cell. The apparatus uses a reference electrode comprising a solid oxygen electrolyte tube containing a reference electrode of a cryolite melt supersaturated with alumina. A measuring electrode is combined with such a reference electrode to provide a potential representative of alumina concentration in the alumina electrolysis cell.

2 Claims, 2 Drawing Figures

APPARATUS FOR DETERMINATION OF ALUMINUM OXIDE CONTENT OF THE CRYOLITE MELT IN ALUMINUM ELECTROLYSIS CELLS

BACKROUND OF THE INVENTION

The invention relates to an apparatus for determination of aluminium oxide content of the cryolite melt in aluminium electrolysis cells comprising an oxygen ion conducting solid electrolyte containing oxygen galvanic cell equipped with a reference electrode of given oxygen potential arranged in a zirconium oxide tube closed on one end and with a measuring electrode covered with aluminium and being in connection with the cryolite melt.

It is known that the current efficiency can be inreased by keeping the appropriate alumina concentration in the course of aluminium electrolysis and, thus, it is an important economical aspect.

Measuring of the alumina in an aluminium electrolysis cell is done almost exclusively by classical analytical methods after sampling. This is very slow and cumbersome and therefore there is no chance to intervene quickly in the technology. The instrumental analytical methods—x-ray diffraction and microscope—works only on the basis of a previous sampling.

The aluminium oxide content of cryolite melts has been evaluated by electrochemical methods. Such a procedure is described in the Hungarian Pat. No. 175438. In this case the electrolytic potential is increased on a graphite electrode of known surface and this results in the increase of the current density. The $Al_2O_3$ concentration of the cryolite melt can be calculated from the actual anodic marginal current. This is an intermittent method and the data obtained are characteristic only in a short time interval.

Further disadvantage of this method is that the use of a polarizing unit is necessary for the operation and polarization programs should be started and run in each test.

The apparatus described in the German patent applications No. 1 798 248, No. 1 798 307 and No. 23 50 485 measure the oxygen content of the melts by means of oxygen ion conducting solid electrolyte containing oxygen galvanic cells.

These apparatus contain zirconium oxide tubes with reference electrodes therein. The electrodes are materials of different oxygen potential, for example, a mixture of metal and metal oxide; gases, for example air, etc. The measuring electrode is a conductor usually fitted onto the outer surface of the zirconium oxide tube or placed beside it. The conductor has a covering which makes possible the transmission of electrons.

In spite of its simplicity, this apparatus is suitable for continous measuring. Its disadvantage is, however, that it is difficult to keep the advantageous oxygen potential of the reference electrode. In case of gases the constant oxygen potential while in case of other reference materials the choice of material producing appropriate results and the assembly of the electrode are the problems.

There are difficulties also with the measuring electrode and with its covering especially in case of melts at high temperature. In case of cryolite melts the conductor has to be covered with aluminium, but at high temperature it gets damaged very quickly and forms more interfaces which cause inaccuracy in the measuring.

SUMMARY OF THE INVENTION

Therefore the object of the present invention is to provide an apparatus which measures simply and continously the aluminium oxide content of the cryolite melt in the electrolysis cell, the preparation of which is simple and contains reliable electrodes.

The apparatus according to the invention is an oxygen ion conducting solid electrolyte containing oxygen galvanic cell equipped with a reference electrode of given oxygen potential arranged in a zirconium oxide tube closed on one end and with a measuring electrode covered with aluminium and being in connection with the cryolite melt. The reference electrode according to the invention is cryolite melt supersaturated with $Al_2O_3$ while the aluminium coating of the measuring electrode is the molten aluminium of the furnace into which the electrode is immersed.

Practically the conductor of the measuring electrode is covered with boron nitride protective coating.

The apparatus can be used under technological conditions as a probe which provides high accuracy and comfort even at high temperature and in a contaminated environment.

There are no special requirements to meet with the probe in order to provide accuracy, that means there is need to define exactly the surface of the measuring electrode, because the aluminium melt itself forms the surface and choosing the potential of this melt the average concentration of the aluminium oxide can be measured well.

DESCRIPTION OF THE PREFERRED EMBODIMENTS

Figure 1:
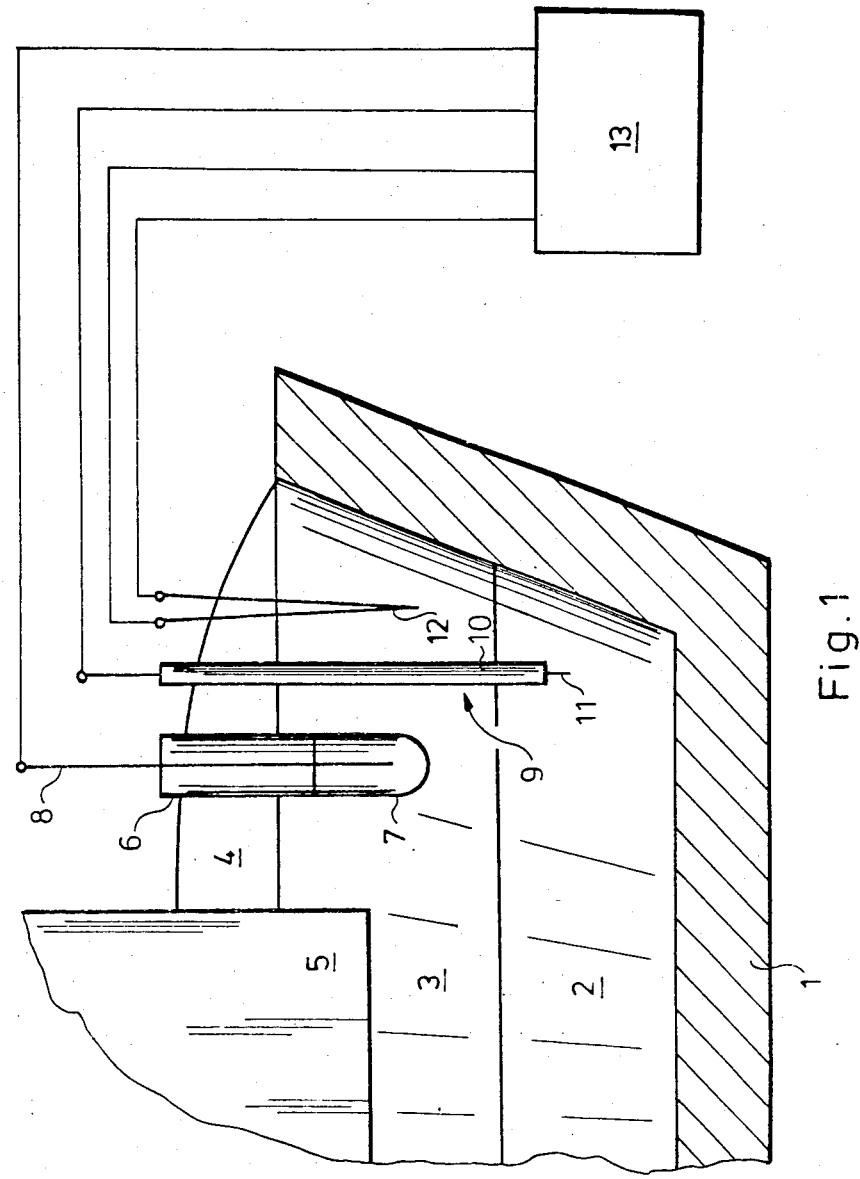
FIG. 1 shows the schematic illustration of the apparatus under technological conditions.

On the FIG. 1, on the bottom of an electrolysis cell /1/ there is the aluminium melt /2/, over it the cryolite-alumina melt (3) is placed while the slag /4/ is on the top. An anode /5/ protrudes into the electrolysis cell /1/. The apparatus according to the invention is shown under technological conditions. From the left a reference electrode /7/ and the current supplying wire /8/ can be seen, both are placed in a solid electrolyte tube /6/.

In the middle the measuring electrode /9/ can be seen in the form of a conductor /11/ covered with a protective coating /10/.

From the right a thermocouple /12/ measuring the temperature is located.

The eletrodes /7 and 9/ and the thermocouple /12/ are connected to the same instrument /13/.

The solid electrolyte /6/ which contains the reference electrode /7/ is in zirconium oxide tube closed at one end forming this way an oxygen ion permissive container. The cryolite and the appropriate amount of alumina is poured into this container. The appropriate amount means that the cryolite melt should be supersaturated with $Al_2O_3$. It can be realized very simply with the overcharge of the alumina. This way adjustment and control are not necessary. The current supplying wire /8/ protrudes into the so obtained reference electrode /7/ and, at the other end it is connected to the instrument /13/. The solid electrolyte /6/ is fitted by its upper part to a boron nitride tube which is cryolite-resistant.

The so obtained electrode can work for more hours even in a very corrosive melt which is characteristic for the alumina electrolysis. Therefore it is suitable for continous measuring.

The lead-in wire /11/ covered with the protective coating /10/ forms the measuring electrode /9/, where the lead-in wire /11/ is made of molybdenum. The protective coating /10/ is made of boron nitride, thus also the measuring electrode /9/ is resistant to corrosion.

To sum up, the present invention provides an apparatus being a galvanic cell, where with alumina saturated cryolite melt and the aluminium forms the reference electrode and the aluminium melt itself forms the measuring electrode as the measuring electrode /9/ protrudes into the molten aluminium /2/. The reference electrode /7/ and the thermocouple /12/ are placed in the cryolite-alumina bath /3/ layer.

In the course of measuring it is possible to register the change of electromotive force and the $Al_3O_3$ content is calculated from it with following formula:

$$E_{MF} = E° - (RT)/(GF) \ln /\%Al_2O_3/$$

where $E_{MF}$ = the measured electromotive force /V/
$E°$ = the electromotive force /V/ in the 1 m % cryolite melt at T temperature
R = the molar gas constant /8,31433 J mol$^{-1}$K$^{-1}$/
F = Faraday constant /96487 C mol$^{-1}$/

Figure 2:
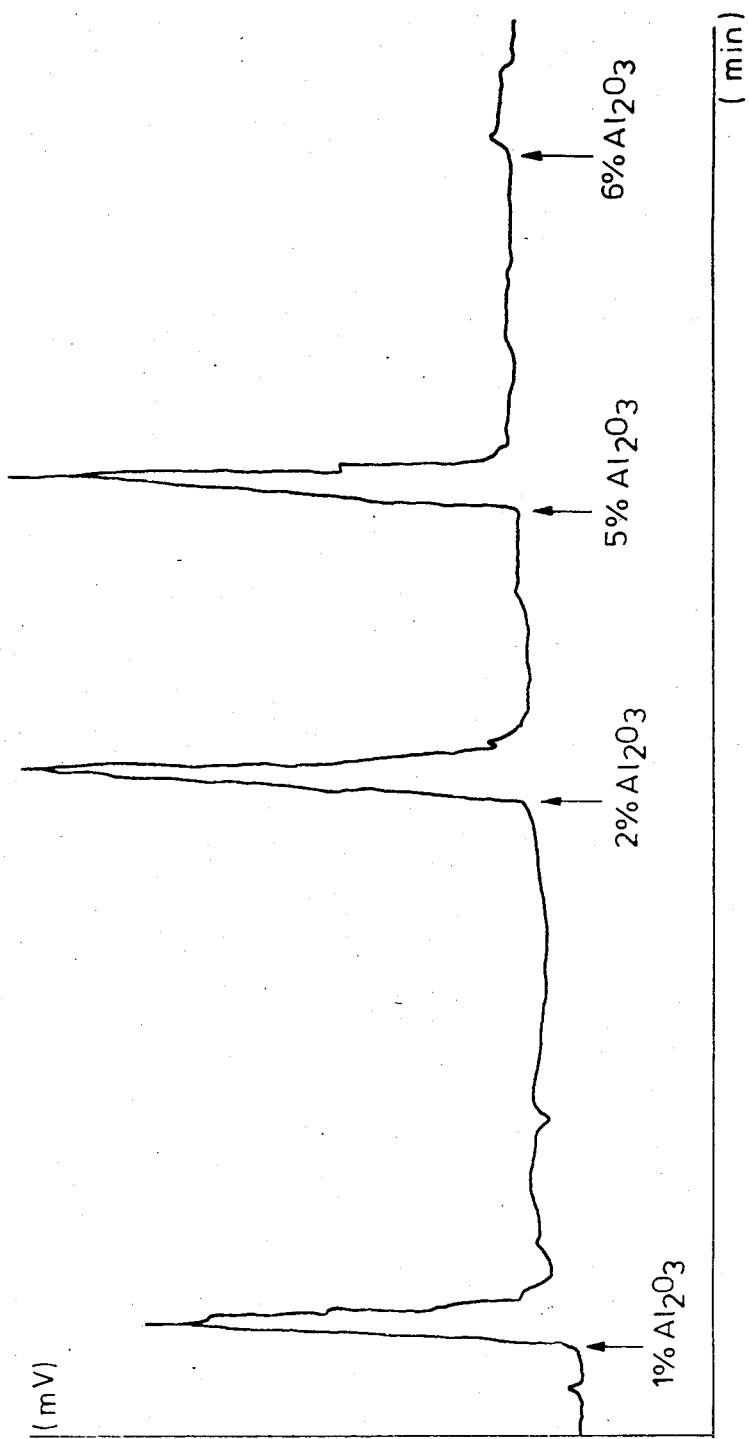
FIG. 2 shows the diagram obtained by means of the apparatus.

FIG. 2 shows the diagram obtained under technological conditions. This Figure shows how $E_{MF}$ changes versus time when under intensive stirring we increase the aluminium oxide content of the 1 m.% aluminium oxide containing cryolite melt by adding additionally aluminium oxide. Because of the sensitive probe we observe a sudden change of electromotive force after adding 1% $Al_2O_3$ to the cryolite melt. After dissolution of alumina a steady state develops, the level of which is higher than before the peak. Adding 2% aluminium oxide the reaction is analogous but the difference between the level of the steady state e.m.f /because of the less concentration difference between the parts divided by the $ZrO_2$ probe/ will be less.

It can be seen that the change of the e.m.f. is minimal at 5% and 6%.

For the industrial point of view the measuring of this difference is sufficient, because it makes it unambiguously possible to determine whether the alumina concentration in the electrolysis cell is low /2-3%/ or high /5-6%/.

Generally it is sufficient to know the alumina concentration in the electrolysis cell quantitatively. Knowing the calibration curve relating to the e.m.f and the concentration of aluminium oxide the unknown concentration can be measured.

The above example shows that the apparatus according to the invention can be used simply, safely, relatively long lasting and continously for the determination of the aluminium oxide content of the cryolite melt.

The main advantage of the invention is the simple construction of electrodes. The reference electrode—as it has been mentioned before—can be filled with the cryolite melt from the electrolysis cell and adding of alumina is necessary. The so obtained electrode can be prepared on the spot safely, very quickly without any measuring.

The preparation of the measuring electrode is less difficult, it is enough to immerse the current supplying wire covered with protective coating into the aluminium melt and the electrode works.

With this method the measuring of the spatial inhomogenities of the aluminium oxide at different points in the electrolyte helps to develop the optimum construction of the electrolyzer cell and to determine the optimum place of input of aluminium oxide.

The speed of measuring enables to observe the dissolution of aluminium oxide in the cryolite after the crust-breaking and alumina charging. It is possible this way to find the technologically most appropriate quality of alumina While several embodiments of the invention have been shown and described, it will be apparent to those skilled in the art that modifications may be made therein without departing from the scope of the invention.

What we claim is:

1. An apparatus for determination of aluminium oxide content of a cryolite melt in aluminium electrolysis cells comprising an oxygen ion conducting solid electrolyte containing oxygen galvanic cell equipped with a reference electrode of given oxygen potential arranged in a zirconium oxide tube closed on one end and with a measuring electrode covered with aluminium, said measuring electrode comprising a conductor, said reference electrode being a cryolite melt supersaturated with $Al_2O_3$ and the aluminium coating of the measuring electrode being the aluminium melt in the cell into which the conductor of the electrode protrudes.

2. The apparatus as claimed in claim 1 wherein at least a portion of the the conductor of the measuring electrode has a boron nitride protective coating.

* * * * *